(12) United States Patent
Lecocq et al.

(10) Patent No.: US 7,741,502 B2
(45) Date of Patent: Jun. 22, 2010

(54) METHOD OF MANUFACTURING ALCOHOL ESTERS FROM TRIGLYCERIDES AND ALCOHOLS USING HETEROGENEOUS CATALYSTS BASED ON PHOSPHATE OR AN ORGANOPHOSPHOROUS COMPOUND OF A GROUP 4 METAL

(75) Inventors: Vincent Lecocq, Brignais (FR); Sylvie Maury, Charly (FR); Delphine Bazer-Bachi, Saint Genis Laval (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 118 days.

(21) Appl. No.: 12/101,403

(22) Filed: Apr. 11, 2008

(65) Prior Publication Data

US 2008/0257781 A1   Oct. 23, 2008

(30) Foreign Application Priority Data

Apr. 12, 2007   (FR) .................................. 07 02675

(51) Int. Cl.
*C07C 51/00* (2006.01)
(52) U.S. Cl. .................................... 554/167
(58) Field of Classification Search .................. 554/167
See application file for complete search history.

(56) References Cited

U.S. PATENT DOCUMENTS 3,416,884 A   12/1968   Stynes

2004/0007532 A1   1/2004   Bortun

FOREIGN PATENT DOCUMENTS

| FR | 2 698 101 A | 5/1994 |
| WO | WO 2005/ 021697 A | 3/2005 |
| WO | WO2005021697 | * 10/2005 |

OTHER PUBLICATIONS

De Filippis P. et al: "Transesterification Catalyzed by Sodium Phosphates" Energy & Fuels, The Society, Washington, DC, US vol. 19, No. 6, 2005 pp. 2225-2228, XP003010535.
Demirbase et al: "Biodiesel Production From Vegetable Oils Via Catalytic and Non-Catalytic Supercritical Methanol Transesterification Methods" Process in Energy and Combustion Science, Elsevier Science Publishers, Amsterdam, NL vol. 31, No. 5-6, 2005, pp. 466-487, XP005213717.
Kamiya Y "Zirconium Phosphate With a High Surface Area as a Water-Tolerant Solid Acid" Catalysis Letters, vol. 94, No. 1-2, pp. 45-47 XP002456899.

\* cited by examiner

*Primary Examiner*—Deborah D Carr
(74) *Attorney, Agent, or Firm*—Millen, White, Zelano & Branigan, P.C.

(57) ABSTRACT

A method of manufacturing a composition of alcohol esters of linear monocarboxylic acids with 6 to 26 carbon atoms from a vegetable or animal oil, neutral or acid, virgin or recycled, with monoalcohols having 1 to 18 carbon atoms, in the presence of a phosphate type catalyst or of an organophosphorous compound of a metal selected from the group made up of zirconium, hafnium and titanium, allows to directly produce, in one or more stages, an ester that can be used as fuel and a pure glycerin.

18 Claims, No Drawings

METHOD OF MANUFACTURING ALCOHOL ESTERS FROM TRIGLYCERIDES AND ALCOHOLS USING HETEROGENEOUS CATALYSTS BASED ON PHOSPHATE OR AN ORGANOPHOSPHOROUS COMPOUND OF A GROUP 4 METAL

FIELD OF THE INVENTION

The present invention relates to a new method of manufacturing alcohol esters of monocarboxylic acids from fatty substances of vegetable or animal origin.

The mainly desired reaction is a transesterification carried out according to reaction path I below and possibly a coupled esterification and transesterification reaction, esterification being achieved according to path II below.

Path I: 1 triglyceride+3 alcohols→3 fatty substance esters+ glycerin

Path I: Fatty acid+alcohol→fatty acid esters+water

Path II: Fatty acid+glycerin→glyceride+water

Fatty substance esters are currently used in many applications as diesel fuels, furnace fuel oils, ecological solvents, base compounds for manufacturing fatty alcohol sulfonates, amides, ester dimers, etc.

In the case of diesel fuel, which is today a major application for fatty substance esters, a certain number of specifications have been established, whose list, limits and methods belong to standard EN 14,214 (2003) currently applicable in Europe. The ester must contain at least 96.5% by mass of esters, at most 0.8% by mass of monoglycerides, at most 0.2% by mass of diglycerides and at most 0.2% by mass of triglycerides, few free fatty acids (<0.5 mg KOH per g) that may be corrosive, less than 0.25% by mass of bonded and free glycerin, and only metals as traces. This involves a precise protocol to obtain the desired purity.

When manufacturing an ester from oil or fat and monoalcohol, depending on the nature of the oil initially used, 10 to 15% by mass of a secondary product, which is glycerin, automatically forms. This glycerin is sold at a high price for various uses, but only when it has a high purity, which is obtained after deep purifications in plants specialized in vacuum distillation.

In short, most commercial ester manufacturing methods lead quite readily to raw products (esters and glycerin) that however have to be deeply purified using various treatments that eventually burden the cost of the conversion.

BACKGROUND OF THE INVENTION

It is known to manufacture methyl esters using conventional means such as homogeneous catalysis with soluble catalysts, such as soda or sodium methylate, by reacting a neutral oil and an alcohol such as methanol (for example JAOCS 61, 343-348 (1984)). A pure product that can be used as fuel and a glycerin meeting the specifications are however obtained only after many stages. In fact, the glycerin obtained is polluted by alkaline salts or alcoholates, so that the glycerin purification plant is almost as costly as the ester manufacturing plant.

Heterogeneous catalysis methods afford the advantage of producing catalyst-free esters and glycerin, which are therefore easily purified. However, it is often difficult to economically obtain both an ester and a glycerin of high purity.

European patent EP-B-0,198,243 describes the manufacture of methyl ester by transesterification of an oil with methanol, using as the catalyst an alumina or a mixture of alumina and of ferrous oxide. However, the liquid hourly space velocity (volume of oil injected/volume of catalyst/hour) is low, the amount of glycerin collected is much less than that theoretically expected and the purity of the esters obtained is rather low (ranging between 93.5% and 98%).

Methods using a catalytic system based on metallic oxides, alone or in combination, deposited or not on an alumina, have been described. Patent FR-B-2,752,242 filed by the applicant describes the use of solid and non soluble catalysts formed from alumina and zinc oxide or zinc aluminate. Patent applications EP-A-1,505,048 and EP-A-1,593,732, also filed by the assignee, describe a method of transesterification of vegetable or animal oils by means of heterogeneous catalysts based on mixtures of alumina and titanium oxides, alumina and zirconium oxide, alumina and antimony oxide or combinations of zinc and titanium oxides, alumina, zinc and titanium oxides, bismuth and titanium oxides or alumina, bismuth and titanium oxides.

Besides these oxide type solids, an increasing number of new basic phases has been used to catalyse the transesterification of oils with alcohols.

By way of example, De Filippis et al. (Energy & Fuels, 2005, 19, 225-228) suggest the use of sodium phosphate for catalysing the rapeseed oil transesterification reaction. Although the authors point out that this type of solid can be reused in two successive cycles with a 1% activity loss, nothing shows that the resistance of the materials is sufficient over long periods of time. In fact, some problems due to the presence of water in the feed are mentioned, notably swelling of these phases and wall adhesion.

Suppes et al. (Applied Catalysis A: general 257 (2004) 213-223) use different materials such as Cs or K-exchanged zeolites or metals that go into the composition of the reactors for transesterification of soybean oil.

SUMMARY OF THE INVENTION

The present invention describes a method of manufacturing a composition of alcohol esters of linear monocarboxylic acids with 6 to 26 carbon atoms and glycerin, wherein a fatty substance of animal or vegetable origin is reacted with an aliphatic monoalcohol having 1 to 18 carbon atoms, in the presence of at least one basic heterogeneous catalyst based on phosphate or a phosphonate or diphosphonate type organophosphorous compound of at least one group 4 metal selected from among zirconium, titanium and hafnium.

Phosphates or phosphonate or diphosphonate type organophosphorous compounds of group 4 metals are multifunctional lamellar solids that can be used for ion exchange, catalysis, as catalytic support or adsorbent.

One advantage of the invention using catalysts based on phosphates or phosphonate or diphosphonate type organophosphorous compounds of at least one metal selected from among zirconium, titanium or hafnium is the capacity thereof to catalyse the transesterification of fatty substances with alcohols heavier than methanol. Thus, it is possible to form ethyl, isopropyl or butyl esters, which is of advantage because the pour points of the esters formed with ethyl, isopropyl or butyl alcohols are often lower than those of methyl esters, the gain being sometimes 10° C., which allows more saturated oils to be initially used.

Another advantage of the invention using a catalyst based on phosphate or phosphonate or diphosphonate type organophosphorous compounds of at least one metal selected from among zirconium, titanium or hafnium is notably that it allows to decrease the reaction temperature and the contact time between the reactants and/or the alcohol/fatty substance ratio in relation to the prior art, while improving the conversion ratio and by maintaining a high ester selectivity.

Yet another advantage of the invention lies in the fact that these solids catalyse transesterification and esterification reactions according to a heterogeneous catalysis process. Thus, the catalyst is not consumed in the reaction and is not dissolved in the reaction medium. By remaining in the solid form, it is easily separated from the reaction medium without catalyst loss and without pollution of the reaction medium by dissolved species or catalyst residues.

The activity and the selectivity of this catalyst are not affected by the transesterification or esterification reaction: the catalyst is stable and recyclable under the experimental reaction conditions. This type of catalyst is compatible with a use in a continuous industrial process, with a fixed bed for example, wherein the catalyst feed can be used for a very long time without any activity loss.

The method according to the invention is described more in detail hereafter.

DETAILED DESCRIPTION

Fatty Substances

The fatty substances used in the method according to the invention correspond to natural or elaborate substances, of animal or vegetable origin, predominantly containing triglycerides, commonly termed oil and fats.

Examples of oils that can be used are all the common oils, such as palm oil (concrete or olein), soybean oil, palm nut oil, copra oil, babassu oil, rapeseed oil (old or new), sunflower oil (conventional or oleic), corn oil, cotton oil, peanut oil, pourgher oil (*Jatropha curcas*), castor oil, linseed oil and crambe oil, and all the oils obtained from sunflower and rapeseed for example by genetic engineering or hybridization, or obtained from algae.

It is even possible to use waste kitchen oil, slaughterhouse oil, various animal oils such as fish oil, seal oil, tallow, lard, fat from sewage treatment and even fowl fat, because the esters manufactured from certain alcohols such as ethyl, isopropyl or butyl alcohol allow to gain more than 10° C. in pour point and consequently to initially use more saturated oils.

The oils used can also include partly modified oils, for example by polymerization or oligomerization, such as for example linseed oil or sunflower oil "stand oils", and blown vegetable oils.

The oils used are neutral or acid, virgin or recycled oils.

The presence of fatty acids in the oils is not a priori harmful because catalytic systems based on phosphate or phosphonate or diphosphonate type organophosphorous compounds of group 4 metals are also active for esterification and they also convert fatty acids to esters. The limit value for the free fatty acids contained in oils ranges around an acid number close to 10 (the acid number being defined as the mass in mg of KOH required for determining the proportion of all the free fatty acids in 1 g oil). The operability of the method under such conditions is close to that defined with an oil having a low acid number (i.e. below 0.2 mg KOH/g).

In the case of oils with a very high acid number (close to 10 mg KOH/g), one option consists in preceding the transesterification reaction by an esterification reaction of the free fatty acids present, using either the same alcohol as the alcohol used in the transesterification method in the presence of a strong acid such as sulfuric acid or soluble or supported sulfonic acids (of Amberlyst 15® resins type), or using preferably glycerin, to form a total or partial glycerol ester, using the same catalyst based on phosphates or phosphonate or diphosphonate type organophosphorous compounds of group 4 metals, at atmospheric pressure and preferably under vacuum, and at temperatures ranging between 150° C. and 220° C.

When using waste kitchen oils, which are a very cheap raw product for the production of a biodiesel fuel, the fatty acid polymers have to be removed from the reaction mixture so that the mixture of esters meets the specifications of the EN 14214 standard.

Alcohol

The nature of the alcohol used in the method plays a part in the transesterification activity.

In general terms, it is possible to use various aliphatic monoalcohols having for example 1 to 18 carbon atoms, preferably 1 to 12 carbon atoms.

More preferably, the aliphatic monoalcohol comprises 1 to 5 carbon atoms.

The most active one is methyl alcohol. However, ethyl alcohol and isopropyl, propyl, butyl, isobutyl and even amyl alcohols can be considered. Heavier alcohols such as ethylhexyl alcohol or lauric alcohol can also be used.

Methyl alcohol that facilitates the reaction can advantageously be added to the heavy alcohols.

Furthermore, when preparing the ethyl ester, it is possible to use a mixture of ethyl and methyl alcohol comprising 1 to 50 wt. %, preferably 1 to 10 wt. % methyl alcohol so as to increase the conversion.

Catalysts

Most catalysts come in form of powders, balls, extrudates or pellets. These types of form remain valid in the case of the phosphate, phosphonate or diphosphonate phases as described in the present invention.

If the reactor technology requires catalysts in form of balls, pellets, granules or extrudates, the various forming modes known to the person skilled in the art can be used (impregnation, deposition, mixing-extrusion, granulation, pelletizing . . . ). The examples below illustrate in a non exhaustive way some of the methods that can be considered.

Powders made up of phosphate or phosphonate or diphosphonate type organophosphorous compounds of group 4 metals can be subjected to granulation using, for example, organic or inorganic binders.

The use of binders, feeds, peptization agents also allows forming of extrudates by mixing-extrusion.

It is also possible to carry out spherical forming of zirconia without a binder via the drop coagulation process followed by a modification stage as described in U.S. Pat. No. 6,936,175.

The conventional methods of deposition on suitable preformed supports, impregnation or modification of a preformed support (as described in U.S. Pat. No. 6,936,175 for example), known to the person skilled in the art, can also be advantageously used.

Another forming mode consists in flocculating the solid formed and in drying it so as to obtain granules (U.S. Pat. No. 3,056,647). However, in this case, water remains partly trapped in the solid, which provides physical properties close to those of silica gel.

All these types of forming methods can be carried out in the presence or in the absence of a binder.

Alumina can for example be used as the binder. It allows to increase the surface area of the material and often to create a compound that is much more stable towards leaching and mechanical stresses. Preferably, the alumina content is up to 70 wt. % in relation to the total mass of the formed material.

Examples of zirconium sources are the well-known alkoxide forms $Zr(OR)_4$, R being an alkyl group containing 3 to 18 carbon atoms. It is also possible to use zirconium in the form of inorganic salts ($ZrOCl_2$, $ZrOSO_4$, $ZrO(NO_3)_2$, etc.), zirconium oxides or hydroxides.

Similarly, the colloidal forms of zirconium can be used (colloidal means that the size of the zirconium oxide or hydroxide particles ranges between 1 nm and 100 nm).

Finally, the zirconium sources can be gels obtained from hydrolysis of the previous sources, thus allowing to obtain a partly hydrated form of zirconium oxide of chemical formula ($ZrO_2$, $zH_2O$), z ranging between 0 and 5.

It is also advantageous to use dehydrated zirconium oxide, amorphous or crystallized, which has in the latter case quadratic, monoclinic or cubic crystallographic structures.

Phosphorus sources can have various origins. In general terms, any type of organophosphorous compound having at least one proton donor group (P—OH for example) can be used.

In a non limitative way, it is possible to use phosphoric acid $H_3PO_4$, or phosphoric acid, potassium, sodium, ammonium salts, phosphonic acid derivatives of general formula ROP(OH)$_2$ (R being an alkyl or aryl group, functionalized or not, having 1 to 20 carbon atoms), diphosphonic acid derivatives, pyrophosphates and phosphinates.

The preparation of phosphates or of organophosphorous compounds of phosphonate or diphosphonate type of group 4 metals and notably of zirconium is known from the prior art. It has been the subject of many publications and patents (U.S. Pat. No. 6,936,175 or US-2006/01,400,840). The various synthesis routes leading to these solids are applicable within the scope of the present invention and the preparation modes presented here are in no way restrictive.

This catalyst type can be advantageously prepared using one of the methods described hereafter and known to the person skilled in the art.

A conventional method of preparing an amorphous zirconium phosphate comprises a first stage wherein a reaction occurs between an aqueous solution of a zirconium salt and phosphoric acid (or one of its salts), which leads to the formation of a gelatinous precipitate. After filtering, washing and drying, a white powder or uneven grains are obtained, which can thereafter be used in a second stage wherein an ion exchange is carried out (in a non limitative way, with salts of metals from the group made up of alkalines, alkaline earths or metals, for example sodium, potassium, calcium, magnesium, barium or cesium salts) in order to obtain a basic solid. The exchange is preferably performed with salts of metals from the groups made up of alkalines or alkaline earths, more preferably with potassium salts.

In the first stage of one synthesis route, the acid form of zirconium phosphate $Zr(O_3POH)_2 \cdot 8H_2O$ is to be synthesized. The latter is obtained by reacting a zirconium precursor ($ZrOCl_2 \cdot 8H_2O$) with a phosphoric acid solution either by refluxing the reaction mixture or at ambient temperature under stirring. The solid obtained is then filtered, washed and dried (route 1).

Another synthesis route consists in reacting in a first stage $ZrOCl_2 \cdot 8H_2O$ with $(NH_4)_2CO_3$ by forming a zirconium carbonate complex. Then, the phosphate source $(NH_4)_2HPO_4$ is added and dissolved in the solution in the presence (or not) of a surfactant (tetradecyltrimethylammonium bromide or TTBr) and the solution is kept at 80° C. for 3 days with a view to precipitation. It is eventually filtered, then washed, dried and calcined (route 2).

$ZrOCl_2 \cdot 8H_2O$ can be replaced by zirconium n-propoxide ($Zr(OC_3H_7)_4$) and it can be reacted with phosphoric acid (route 3).

In the second stage, an exchange of the acid form by potassium precursors (KCl, KOH) is carried out. After filtering and washing, followed by a drying stage, the potassium-exchanged zirconium phosphate $Zr(O_3POK)_2$ is finally obtained.

A conventional method of preparing amorphous zirconium phosphonate or diphosphonate comprises the reaction between an aqueous solution of a zirconium salt and phosphonic or diphosphonic acid (or one of its salts).

Thus, it is possible to react the zirconium precursor $ZrOCl_2 \cdot 8H_2O$ with a phosphonic or diphosphonic acid, functionalized or not, and $NaH_2PO_4$ (route 4).

In the case of phosphonates and diphosphonates, the second stage of ion exchange is not systematic and it can occur if the phosphonate or the diphosphonate comprises a functionalized group containing an acid function allowing cation exchange.

Operating Conditions of the Transesterification Reaction

The method is carried out at temperatures ranging between 130° C. and 220° C., at pressures below 100 bars, with excess monoalcohol in relation to the fatty substance/alcohol stoichiometry.

The reaction can generally be operated according to various embodiments.

In the case of a discontinuous reaction, it can be conducted in one or two stages, i.e. carrying out a first reaction up to 85% to 95% conversion to esters, cooling by evaporating the excess alcohol, decanting the glycerin and ending the reaction by heating again to between 130° C. and 220° C. and by adding alcohol to obtain total conversion.

A 98% conversion to esters can also be aimed by working for a sufficiently long time in a single stage under suitable conditions, for example by increasing the temperature and/or the alcohol/fatty substance ratio.

In the case of a continuous reaction, it can be carried out using several autoclaves and decanters. A partial conversion, most often below 90% and generally of approximately 85%, is performed in a first reactor, then decanting is achieved by evaporating the alcohol and by cooling. The transesterification reaction is completed in a second reactor under the aforementioned conditions by adding part of the alcohol previously evaporated. The excess alcohol is finally evaporated in an evaporator and the glycerin and the esters are separated by decantation.

Thus, after these two stages, a biodiesel fuel meeting the specifications is obtained. The conversion level is adjusted so as to obtain an ester fuel meeting the specifications and a glycerin of high purity, by operating in one or two stages.

When selecting a fixed-bed continuous method, it can be advantageous to work at temperatures ranging between 130° C. and 220° C., preferably between 150° C. and 180° C., at pressures ranging between 10 and 70 bars, the LHSV preferably ranging between 0.1 and 3, more preferably between 0.3 and 2, in the first stage and the alcohol/oil weight ratio ranging between 3/1 and 0.1/1.

Alcohol introduction can be advantageously fractionated. Introduction at two levels of the tubular reactor can be done as follows: supplying the reactor with oil and about ⅔ of the alcohol, then introducing the alcohol complement approximately at the level of the upper third of the catalyst bed.

The leaching strength is verified in the present invention by the absence of traces from the catalyst, in the ester formed as well as in the glycerin produced.

The recyclability of the catalyst is experimentally evaluated with time.

If a temperature of 220° C. is not exceeded, the ester obtained has generally the same colour as the initial oil and the glycerin is colourless after decantation.

Analysis of the compounds produced is performed either by gas chromatography for the esters and the glycerin or, more rapidly, by liquid exclusion chromatography for the esters.

The ester and the glycerol obtained contain no impurities from the catalyst. No purification treatment is therefore applied to eliminate the catalyst or residues thereof, unlike catalysts working according to a homogeneous process wherein the catalyst or its residues are, after the reaction, located in the same phase as the ester and/or the glycerin.

The ester fuel obtained has a monoglyceride content of at most 0.8% by mass, a diglyceride content of at most 0.2% by mass, a triglyceride content of at most 0.2% by mass and a glycerine content of less than 0.25% by mass.

By means of this type of process, the final purification is reduced to a minimum while allowing to obtain an ester meeting the fuel specifications and a glycerin whose purity ranges between 95% and 99.9%, preferably between 98% and 99.9%.

EXAMPLES

The following examples illustrate the invention without limiting the scope thereof, examples 5, 7 and 8 being given by way of comparison.

All the examples given below were carried out in a closed reactor and they therefore correspond to a single stage. To obtain a biodiesel fuel meeting the specifications, it would be necessary to perform, at the end of this first stage, a decantation by evaporating the alcohol and by cooling, then to complete the transesterification reaction by adding the evaporated alcohol part.

The oil used in these examples is rapeseed oil whose fatty acid composition is as follows:

TABLE 1

Rapeseed oil composition

| Fatty acid glyceride | Nature of the fatty chain | % by mass |
|---|---|---|
| Palmitic | C16:0 | 5 |
| Palmitoleic | C16:1 | <0.5 |
| Stearic | C18:0 | 2 |
| Oleic | C18:1 | 59 |
| Linoleic | C18:2 | 21 |
| Linoleic | C18:3 | 9 |
| Arachidic | C20:0 | <0.5 |
| Gadoleic | C20:1 | 1 |
| Behenic | C22:0 | <0.5 |
| Erucic | C22:1 | <1 |

However, any other oil of vegetable or animal origin could give similar results.

The catalyst used in examples 1, 3, 5, 6 and 7 was prepared by first reacting a zirconium precursor ($ZrOCl_2 \cdot 8H_2O$) with a phosphoric acid solution (route 1), then by carrying out the ion exchange stage described above in order to obtain the basic phase.

Example 1

Transesterification of Vegetable Oils (Rapeseed Oil) by Methanol from a Solid Catalyst of Zirconium Phosphate Type $Zr(OPO_3K)_2$ at 180° C.

25 g rapeseed oil, 25 g methanol and 1 g catalyst in powder form are fed into a closed reactor at ambient temperature. The methanol/oil mass ratio is thus 1, which corresponds to a molar ratio of 27.5. The reactor is then closed, stirred (200 rpm) and heated to 180° C. by means of a heating magnetic stirrer. The temperature of the reaction medium is stabilized at 180° C. after 20 minutes heating. The pressure is the autogenous pressure of alcohol at the operating temperature. The reaction is monitored as soon as the temperature of the reaction medium has reached the set temperature value. Samples are regularly taken in order to follow the progress of the reaction. After 6 hours reaction, stirring is stopped and the reactor is left to cool down to ambient temperature. The samples taken and the final effluent are washed by means of a NaCl-saturated aqueous solution then, after decantation, the upper organic phase is analysed by gel-permeation chromatography (GPC). The table below shows the results obtained.

|  |  | Samples (in h) | | |
|---|---|---|---|---|
|  |  | $0^b$ | 0.4 | 0.6 |
| % by mass in the organic phase$^a$ | Triglycerides | 26 | 5 | 1 |
|  | Diglycerides$^c$ | 17 | 7 | 3 |
|  | Monoglyceride | 13 | 10 | 5 |
|  | Vegetable oil methyl esters | 44 | 79 | 90 |

$^a$determined by GPC
$^b$t = 0 when the reaction medium is at temperature
$^c$% representing the diglycerides and sterols Conversion of the triglycerides starts whereas the reaction medium has not reached 180° C. (44% esters at t0). Thermodynamic equilibrium is reached very rapidly (approximately 40 minutes) after the reaction medium has reached 180° C. The conversion (estimated in relation to the triglycerides, conversion=$1-m_{final}$(triglycerides)/$m_{initial}$(triglycerides)) is 99% at 40 min.

Leaching of the catalyst in the ester phase is negligible (the phosphorus and potassium content estimated by means of the inductively coupled plasma (ICP) technique is below 5 ppm). This result is valid for all the examples below as regards zirconium phosphates.

Example 2

Transesterification of Vegetable Oils (Rapeseed Oil) by Methanol from a Solid Catalyst of Zirconium Phosphate $Zr(OPO_3K)_2$ Type at 170° C.

Example 1 is repeated using 25 g rapeseed oil, 25 g methanol and 1 g catalyst in powder form. The reaction is carried out at 170° C., the temperature of the reaction medium being stabilized at 170° C. after 20 minutes heating. The table hereafter gives the results obtained.

|  |  | Samples (in h) | | | |
|---|---|---|---|---|---|
|  |  | $0^b$ | 0.4 | 0.6 | 1 |
| % by mass in the organic phase$^a$ | Triglycerides | 48 | 15 | 3 | 1 |
|  | Diglycerides$^c$ | 17 | 11 | 5 | 3 |
|  | Monoglyceride | 9 | 12 | 8 | 5 |
|  | Vegetable oil methyl esters | 26 | 62 | 83 | 90 |

$^a$determined by GPC
$^b$t = 0 when the reaction medium is at temperature
$^c$% representing the diglycerides and sterols Conversion of the triglycerides starts whereas the reaction medium has not reached 170° C. (26% esters at t0). Thermodynamic equilibrium is reached very rapidly (in 60 min approximately). The conversion (estimated in relation to the triglycerides) is 99% at 60 min.

Example 3

Transesterification of Vegetable Oils (Rapeseed Oil) by Methanol from a Solid Catalyst of Zirconium Phosphate Type $Zr(OPO_3K)_2$ at 160° C.

Example 1 is repeated using 25 g rapeseed oil, 25 g methanol and 1 g catalyst in powder form. The reaction is carried out at 160° C., the temperature of the reaction medium being stabilized at 160° C. after 20 minutes heating. The table hereafter gives the results obtained.

|  |  | Samples (in h) | | | |
| --- | --- | --- | --- | --- | --- |
|  |  | $0^b$ | 0.4 | 0.6 | 1.5 |
| % by mass in the organic phase$^a$ | Triglycerides | 47 | 24 | 9 | 1 |
|  | Diglycerides$^c$ | 18 | 15 | 9 | 3 |
|  | Monoglyceride | 7 | 12 | 11 | 5 |
|  | Vegetable oil methyl esters | 28 | 49 | 71 | 90 |

$^a$determined by GPC
$^b$t = 0 when the reaction medium is at temperature
$^c$% representing the diglycerides and sterols Thermodynamic equilibrium is reached very rapidly (in 1.5 h approximately). The conversion (estimated in relation to the triglycerides) is 99% in 1.5 h.

Example 4

Transesterification of Vegetable Oils (Rapeseed Oil) by Methanol from a Solid Catalyst of Zirconium Phosphate Type $Zr(OPO_3K)_2$ at 150° C.

Example 1 is repeated using 25 g rapeseed oil, 25 g methanol and 1 g catalyst in powder form. The reaction is carried out at 150° C., the temperature of the reaction medium being stabilized at 150° C. after 15 minutes heating. The table hereafter gives the results obtained.

|  |  | Samples (in h) | | | |
| --- | --- | --- | --- | --- | --- |
|  |  | $0^b$ | 0.4 | 0.6 | 2.1 |
| % by mass in the organic phase$^a$ | Triglycerides | 69 | 36 | 19 | 1 |
|  | Diglycerides$^c$ | 15 | 18 | 14 | 3 |
|  | Monoglyceride | 4 | 11 | 13 | 5 |
|  | Vegetable oil methyl esters | 12 | 35 | 54 | 90 |

$^a$determined by GPC
$^b$t = 0 when the reaction medium is at temperature
$^c$% representing the diglycerides and sterols The 99% conversion is reached in 2.1 h at 150° C.

Example 5 (Comparative)

Transesterification of Rapeseed Oil by Methanol in the Presence of Zinc Aluminate ($ZnAl_2O_4$) in Powder Form at 150° C.

Example 1 is repeated using 25 g rapeseed oil, 25 g methanol and 1 g catalyst in powder form. The reaction is carried out at 150° C., the temperature of the reaction medium being stabilized at 150° C. after 15 minutes heating. The table below gives the results obtained.

|  |  | Samples (in h) | | |
| --- | --- | --- | --- | --- |
|  |  | $0^b$ | 4 | 6 |
| % by mass in the organic phase$^a$ | Triglycerides | 94 | 69 | 61 |
|  | Diglycerides$^c$ | 4 | 17 | 19 |
|  | Monoglyceride | 0 | 2 | 3 |
|  | Vegetable oil methyl esters | 2 | 12 | 16 |

$^a$determined by GPC
$^b$t = 0 when the reaction medium is at temperature
$^c$% representing the diglycerides and sterols This example clearly shows that the zinc aluminate catalyses the transesterification reaction much more slowly than a zirconium phosphate since the 99% conversion is reached only after 60 h.

Example 6

Transesterification of Vegetable Oils (Rapeseed Oil) by Methanol from a Solid Catalyst of Zirconium Phosphate Type $Zr(OPO_3K)_2$ at 140° C.

Example 1 is repeated using 25 g rapeseed oil, 25 g methanol and 3 g catalyst in powder form. The reaction is carried out at 140° C., the temperature of the reaction medium being stabilized at 140° C. after 30 minutes heating. The table below gives the results obtained.

|  |  | Samples (in h) | | |
| --- | --- | --- | --- | --- |
|  |  | $0^b$ | 4 | 6 |
| % by mass in the organic phase$^a$ | Triglycerides | 19 | 0 | 0 |
|  | Diglycerides$^c$ | 8 | 2 | 2 |
|  | Monoglyceride | 8 | 4 | 4 |
|  | Vegetable oil methyl esters | 64 | 94 | 94 |

$^a$ determined by GPC
$^b$t = 0 when the reaction medium is at temperature
$^c$% representing the diglycerides and sterols This example shows that increasing the catalyst mass allows to work at lower temperatures while having a total conversion very rapidly (less than 4 h).

Example 7

(Not According to the Invention): Transesterification of Vegetable Oils (Rapeseed Oil) by Methanol from a Solid Catalyst of Acid Zirconium Phosphate Type at 200° C.

Example 1 is repeated using 25 g rapeseed oil, 25 g methanol and 3 g catalyst in powder form. The reaction is carried out at 200° C., the temperature of the reaction medium being stabilized at 200° C. after 40 minutes heating. The table below gives the results obtained.

|  |  | Samples (in h) | | |
|---|---|---|---|---|
|  |  | $0^b$ | 4 | 6 |
| % by mass in the organic phase$^a$ | Triglycerides | 93 | 45 | 27 |
|  | Diglycerides$^c$ | 5 | 25 | 26 |
|  | Monoglyceride | 0 | 7 | 12 |
|  | Vegetable oil methyl esters | 2 | 23 | 35 |

$^a$determined by GPC
$^b$t = 0 when the reaction medium is at temperature
$^c$% representing the diglycerides and sterols The activity of the acid form is very low because only 35% esters are obtained after 6 hours reaction, at 200° C. and with 3 g solid. This proportion of esters approximately corresponds to that obtained in the absence of catalyst (purely thermal catalysis). The acid form of the zirconium phosphate is therefore very weakly active.

Example 8 (Comparative)

Transesterification of Vegetable Oils (Rapeseed Oil) by Methanol from Magnesium Oxide MgO at 150° C.

Example 5 is repeated using 25 g rapeseed oil, 25 g methanol and 1 g catalyst in powder form. The reaction is carried out at 150° C., the temperature of the reaction medium being stabilized at 150° C. after 20 minutes heating. The table below gives the results obtained.

|  |  | Samples (in h) | | |
|---|---|---|---|---|
|  |  | $0^b$ | 4 | 6 |
| % by mass in the organic phase$^a$ | Triglycerides | 83 | 5 | 1 |
|  | Diglycerides$^c$ | 10 | 6 | 3 |
|  | Monoglyceride | 1 | 8 | 5 |
|  | Vegetable oil methyl esters | 5 | 80 | 91 |

$^a$determined by GPC
$^b$t = 0 when the reaction medium is at temperature
$^c$% representing the diglycerides and sterols This example clearly shows that the magnesium oxide catalyses the reaction much more slowly than a zirconium phosphate since the 99% conversion is reached only after 6 h.

Example 9

Influence of the Methanol/Oil Molar Ratio R=27.5

The previous examples were carried out with a methanol/oil mass ratio of 1, which actually corresponds to a molar ratio of 27.5. The following examples illustrate the influence of this ratio on the catalytic activity of a catalyst of zirconium phosphate type and they emphasize the good performances of the catalyst even at low ratios.

Example 1 is repeated using 25 g rapeseed oil, 25 g methanol and 1 g catalyst in powder form. The reaction is carried out at 160° C., the temperature of the reaction medium being stabilized at 160° C. after 22 minutes heating. The table below gives the results obtained.

|  |  | Samples (in h) | | | |
|---|---|---|---|---|---|
|  |  | $0^b$ | 0.4 | 0.6 | 2 |
| % by mass in the organic phase$^a$ | Triglycerides | 39 | 11 | 2 | 0.1 |
|  | Diglycerides$^c$ | 19 | 9 | 4 | 2 |
|  | Monoglyceride | 10 | 12 | 7 | 4 |
|  | Vegetable oil methyl esters | 31 | 68 | 87 | 94 |

$^a$determined by GPC
$^b$t = 0 when the reaction medium is at temperature
$^c$% representing the diglycerides and sterols With a molar ratio of R=27.5, the conversion is 98% in 40 min.

Example 10

Influence of the Methanol/Oil Molar Ratio R=20

Example 9 is repeated using 28.9 g rapeseed oil, 21.1 g methanol and 1 g catalyst in powder form. The reaction is carried out at 160° C., the temperature of the reaction medium being stabilized at 160° C. after 22 minutes heating. The table hereafter gives the results obtained.

|  |  | Samples (in h) | | | |
|---|---|---|---|---|---|
|  |  | $0^b$ | 0.4 | 0.6 | 2 |
| % by mass in the organic phase$^a$ | Triglycerides | 52 | 24 | 10 | 0.3 |
|  | Diglycerides$^c$ | 20 | 17 | 10 | 2 |
|  | Monoglyceride | 6 | 13 | 13 | 6 |
|  | Vegetable oil methyl esters | 21 | 46 | 66 | 92 |

$^a$determined by GPC
$^b$t = 0 when the reaction medium is at temperature
$^c$% representing the diglycerides and sterols With R=20, the conversion is 90% in 40 min, and it is nearly total in less than 2 hours.

Example 11

Influence of the Methanol/Oil Molar Ratio R=14

Example 9 is repeated using 33.1 g rapeseed oil, 16.8 g methanol and 1 g catalyst in powder form. The reaction is carried out at 160° C., the temperature of the reaction medium being stabilized at 160° C. after 22 minutes heating. The table below gives the results obtained.

|  |  | Samples (in h) | | | |
|---|---|---|---|---|---|
|  |  | $0^b$ | 0.4 | 0.6 | 2 |
| % by mass in the organic phase$^a$ | Triglycerides | 60 | 33 | 20 | 2 |
|  | Diglycerides$^c$ | 18 | 19 | 15 | 4 |
|  | Monoglyceride | 5 | 12 | 14 | 10 |
|  | Vegetable oil methyl esters | 17 | 36 | 50 | 84 |

$^a$determined by GPC
$^b$t = 0 when the reaction medium is at temperature
$^c$% representing the diglycerides and sterols With R=14, the conversion is 80% in 40 min, and it remains nearly total (98%) in two hours.

Example 12

Influence of the Methanol/Oil Molar Ratio R=10

Example 9 is repeated using 36.7 g rapeseed oil, 13.3 g methanol and 1 g catalyst in powder form. The reaction is carried out at 160° C., the temperature of the reaction medium being stabilized at 160° C. after 22 minutes heating. The table below gives the results obtained.

|  |  | Samples (in h) | | | |
|---|---|---|---|---|---|
|  |  | 0[b] | 0.4 | 0.6 | 2 |
| % by mass in the organic phase[a] | Triglycerides | 69 | 45 | 30 | 6 |
|  | Diglycerides[c] | 16 | 20 | 19 | 9 |
|  | Monoglyceride | 3 | 9 | 13 | 15 |
|  | Vegetable oil methyl esters | 12 | 25 | 38 | 70 |

[a]determined by GPC
[b]t = 0 when the reaction medium is at temperature
[c]% representing the diglycerides and sterols With a methanol/oil molar ratio of 10, the conversion is 70% in 40 min, and 96% in 2 hours. This low ratio does therefore not allow to reach total conversion in 2 hours. However, the catalytic system remains faster than with a catalyst based on MgO or on a zinc aluminate using a large excess of methanol (R=27.5).

Example 13

Influence of the Nature of the Alcohol

Example 1 is repeated using 25 g rapeseed oil, 25 g ethanol and 3 g catalyst of zirconium phosphate type in powder form. The reaction is carried out at 200° C., the temperature of the reaction medium being stabilized at 200° C. after 60 minutes heating. The table below gives the results obtained.

|  |  | Samples (in h) | | |
|---|---|---|---|---|
|  |  | 0[b] | 4 | 6 |
| % by mass in the organic phase[a] | Triglycerides | 59 | 1 | 0.1 |
|  | Diglycerides[c] | 20 | 4 | 3 |
|  | Monoglyceride | 5 | 13 | 9 |
|  | Vegetable oil methyl esters | 16 | 81 | 88 |

[a]determined by GPC
[b]t = 0 when the reaction medium is at temperature
[c]% representing the diglycerides and sterols After 6 hours reaction, the conversion is total and the ethyl esters yield is 88%.

Example 14

Influence of the Nature of the Alcohol

Example 13 is repeated using 25 g rapeseed oil, 25 g ethanol and 3 g catalyst of zirconium phosphate type in powder form. The reaction is carried out at 180° C., the temperature of the reaction medium being stabilized at 180° C. after 30 minutes heating. The table hereafter gives the results obtained.

|  |  | Samples (in h) | | |
|---|---|---|---|---|
|  |  | 0[b] | 4 | 6 |
| % by mass in the organic phase[a] | Triglycerides | 83 | 13 | 4 |
|  | Diglycerides[c] | 11 | 14 | 7 |
|  | Monoglyceride | 1 | 17 | 17 |
|  | Vegetable oil methyl esters | 5 | 56 | 72 |

[a]determined by GPC
[b]t = 0 when the reaction medium is at temperature
[c]% representing the diglycerides and sterols After 6 hours reaction, the conversion is 96% at 180° C., and the ethyl esters yield is 72%.

The preceding examples can be repeated with similar success by substituting the generically or specifically described reactants and/or operating conditions of this invention for those used in the preceding examples.

The entire disclosures of all applications, patents and publications, cited herein and of corresponding French application Ser. No. 07/02675, filed Apr. 12, 2007 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of manufacturing a composition of alcohol esters of linear monocarboxylic acids with 6 to 26 carbon atoms and glycerin, comprising reacting a fatty substance of vegetable or animal origin with an aliphatic monoalcohol having 1 to 18 carbon atoms, in the presence of at least one basic heterogeneous catalyst comprising a phosphate, phosphonate, diphosphonate or organophosphorous compound of at least one group 4 metal selected from zirconium, hafnium and titanium.

2. A method as claimed in claim 1, wherein said aliphatic monoalcohol comprises 1 to 12 carbon atoms.

3. A method as claimed in claim 1, wherein the mono alcohol comprises a mixture of ethyl and methyl alcohol, comprising 1 to 50 wt. % methyl alcohol.

4. A method as claimed in claim 1, conducted at a temperature between 130° C. and 220° C., a pressure below 100 bars, and with excess monoalcohol in relation to fatty substance/alcohol stoichiometry.

5. A method as claimed in claim 1, comprising reacting at least one of palm oil (concrete or olein), soybean oil, palm nut oil, copra oil, babassu oil and rapeseed, sunflower oil, conventional or oleic, corn oil, cotton oil, peanut oil, pourgher oil, castor oil, linseed oil or crambe oil, oils obtained from algae or sunflower or rapeseed oil obtained by genetic engineering or hybridization, or oils partly modified by polymerization or oligomerization, with said monoalcohol.

6. A method as claimed in claim 1, wherein the fatty substance comprises at least one waste kitchen oil, slaughterhouse oil, fish oil, seal oil, fowl fat, tallow, lard, fat from sewage treatment.

7. A method as claimed in claim 1, wherein said catalyst further comprises a binder of alumina in proportions up to 70 wt. % of the total catalyst.

8. A method as claimed in claim 1, wherein said group 4 metal comprises zirconium.

9. A method as claimed in claim 1, wherein the catalyst comprises a basic zirconium phosphate.

10. A method as claimed in claim 1, wherein the catalyst comprises a basic zirconium phosphonate or diphosphonate.

11. A method as claimed in claim 1, wherein the catalyst comprises $Zr(O_3POK)_2$.

12. A method as claimed in claim 11, wherein the reaction is carried out in a fixed bed, at a pressure ranging between 10 and 70 bars and at an LHSV ranging between 0.1 and 3, with an alcohol/fatty substance weight ratio ranging between 3/1 and 0.1/1.

13. A method as claimed in claim 1, wherein the reaction is carried out in one or two stages by adjusting the conversion level so as to obtain an ester fuel having a monoglyceride content of at most 0.8% by mass, a diglyceride content of at most 0.2% by mass, a triglyceride content of at most 0.2% by mass and a glycerin content of less than 0.25% by mass.

14. A method as claimed in claim 1, wherein the reaction is carried out in one or two stages by adjusting the conversion level so as to obtain a glycerin with a purity ranging between 95% and 99.9%.

15. A method according to claim 14, conducted so as to obtain a glycerine purity ranging between 98% and 99.9%.

16. A method according to claim 3, wherein the mixture of methyl and ethyl alcohol comprises 1 to 10% by weight of methyl alcohol.

17. A method according to claim 11, further comprising a preceding step of preparing $Zr(O_3POK)_2$ by a process comprising reacting $ZrOCl_2.8H_2O$ with a phosphoric acid solution, and then conducting ion exchange on the resultant product with a potassium compound.

18. A method according to claim 1, wherein said at least one group 4 metal is hafnium.

* * * * *

UNITED STATES PATENT AND TRADEMARK OFFICE
CERTIFICATE OF CORRECTION

PATENT NO. : 7,741,502 B2
APPLICATION NO. : 12/101403
DATED : June 22, 2010
INVENTOR(S) : Lecocq et al.

It is certified that error appears in the above-identified patent and that said Letters Patent is hereby corrected as shown below:

Column 14, line 53 reads "oil, copra oil, babassu oil and rapeseed, sunflower oil, con-" should read -- oil, copra oil, babassu oil and rapeseed oil, sunflower oil, con- --

Signed and Sealed this

Seventh Day of September, 2010

David J. Kappos
*Director of the United States Patent and Trademark Office*